US009834738B2

(12) United States Patent
Narula et al.

(10) Patent No.: US 9,834,738 B2
(45) Date of Patent: *Dec. 5, 2017

(54) OCTAHYDRO-1H-4,7-METHANO-INDENE-5-ALDEHYDES AND THEIR USE IN PERFUME COMPOSITIONS

(71) Applicant: International Flavors & Fragrances Inc., Union Beach, NJ (US)

(72) Inventors: Anubhav P. S. Narula, Hazlet, NJ (US); James Anthony Lasome, Matawan, NJ (US); Richard A. Weiss, Livingston, NJ (US); Michael G. Monteleone, Hazlet, NJ (US)

(*) Notice: Subject to any disclaimer, the term of this patent is extended or adjusted under 35 U.S.C. 154(b) by 292 days.

This patent is subject to a terminal disclaimer.

(21) Appl. No.: 14/105,404

(22) Filed: Dec. 13, 2013

(65) Prior Publication Data

US 2014/0107220 A1    Apr. 17, 2014

Related U.S. Application Data

(63) Continuation of application No. 13/287,594, filed on Nov. 2, 2011, now Pat. No. 8,633,144.

(51) Int. Cl.
| | | |
|---|---|---|
| C11B 9/00 | (2006.01) |
| A61Q 13/00 | (2006.01) |
| C07C 47/115 | (2006.01) |
| C07C 47/347 | (2006.01) |
| C07C 47/445 | (2006.01) |
| C11D 3/50 | (2006.01) |
| A61K 8/35 | (2006.01) |

(52) U.S. Cl.
CPC ............... *C11B 9/0049* (2013.01); *A61K 8/35* (2013.01); *A61Q 13/00* (2013.01); *C07C 47/115* (2013.01); *C07C 47/347* (2013.01); *C07C 47/445* (2013.01); *C11B 9/0042* (2013.01); *C11D 3/50* (2013.01); *C07C 2103/66* (2013.01)

(58) Field of Classification Search
CPC ..... A61Q 13/00; C07C 47/115; C07C 47/347; C07C 47/445; C11B 9/0042; C11B 9/0049; C11D 3/50
See application file for complete search history.

(56) References Cited

U.S. PATENT DOCUMENTS 5,492,887 A * 2/1996 Brunke ................. C07C 47/347
                                                          512/16
8,633,144 B2 * 1/2014 Narula ................... A61Q 13/00
                                                          510/105

FOREIGN PATENT DOCUMENTS

EP    1591514 A2 * 11/2005
JP    54144353    * 11/1979

OTHER PUBLICATIONS

English Translation of JP-54144353 abstract.*
Machine English Translation of EP-1591514.*

* cited by examiner

*Primary Examiner* — Kara R McMillian
(74) *Attorney, Agent, or Firm* — XuFan Tseng; Martin Zhang; Elizabeth M Stover

(57) ABSTRACT

The present invention is directed to a novel fragrance compound of octahydro-4,7-methano-1H-indene-5-acetaldehyde.

12 Claims, No Drawings

OCTAHYDRO-1H-4,7-METHANO-INDENE-5-ALDEHYDES AND THEIR USE IN PERFUME COMPOSITIONS

STATUS OF RELATED APPLICATIONS

This application is a continuation of U.S. Ser. No. 13/287,594, filed Nov. 2, 2011, now issued into U.S. Pat. No. 8,633,144, the contents hereby incorporated by references as if set forth in their entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor hedonic notes and characteristics of molecules. These variations allow perfumers and other persons to apply new compounds in creating new fragrances with unique and differentiating performance.

For instance, it is well known analogs such as aldehydes and aldehyde derivatives may possess distinct and unique olfactory properties. 3,7-Dimethyl-6-octenal (Citronellal), for example, possesses citrus, green, fruity, and rose scent and has been widely used in both fragrances and flavors. However, its ketone derivative 4,8-dimethyl-7-nonen-2-one, though described as having coconut rosaceous odor since the 1970's, is not suitable for use in fragrances or flavors due to additional undesirable properties such as fatty, stemmy, and weak [Sethi, et al., 22(4): 225-228 (1978)]. Thus, identifying desirable fragrance chemicals continues to pose difficult challenges and predicting odors remains empirical in nature.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to novel octahydro-1H-4,7-methano-indene-5-aldehydes represented by the formulas set forth below:

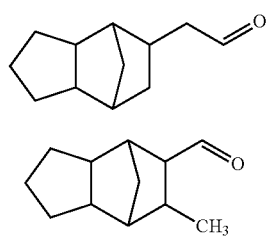

Formula I

Formula II wherein Formula I represents octahydro-4,7-methano-1H-indene-5-acetaldehyde; and Formula II represents octahydro-6-methyl-4,7-methano-1H-indene-5-carboxaldehyde.

Another embodiment of the invention is directed to a fragrance formulation comprising an octahydro-1H-4,7-methano-indene-5-aldehyde compound provided above or a mixture thereof.

Another embodiment of the invention is directed to a method for enhancing a perfume composition by incorporating an olfactory acceptable amount of an octahydro-1H-4,7-methano-indene-5-aldehyde compound provided above or a mixture thereof.

These and other embodiments of the present invention will be apparent by reading the following specification.

DETAILED DESCRIPTION OF THE INVENTION

Those with the skill in the art will appreciate that Formula I above represents octahydro-4,7-methano-1H-indene-5-acetaldehyde; and Formula II above represents octahydro-6-methyl-4,7-methano-1H-indene-5-carboxaldehyde.

The compounds of the present invention can be prepared from octahydro-4,7-methano-inden-5-one according to the reaction scheme below, the details of which are specified in the Examples. Materials were purchased from Aldrich Chemical Company unless noted otherwise.

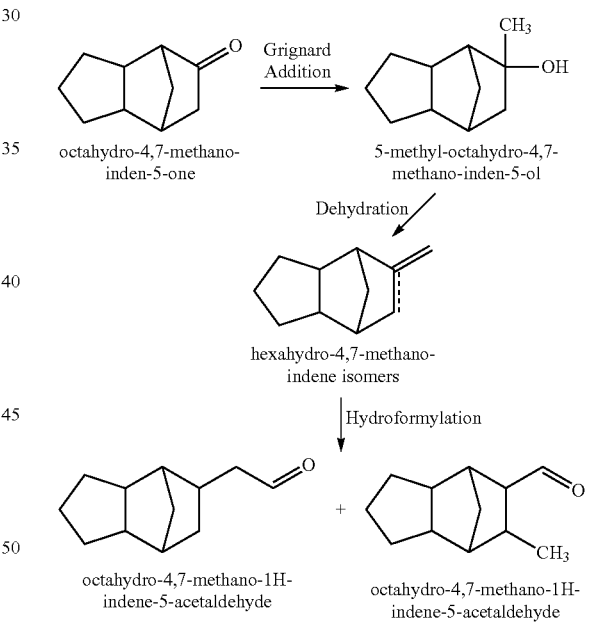

Those with skill in the art will recognize that the product mixture obtained as described above can be separated using techniques known to those with skill in the art. Suitable techniques include, for example, distillation and chromatography such as high performance liquid chromatography, referred to as HPLC, particularly silica gel chromatograph, and gas chromatography trapping known as GC trapping. Yet, commercial products are mostly offered as isomeric mixtures.

Those with skill in the art will further recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art as described above.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1] hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo [7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides fruity, sweet, and green notes to make the fragrance formulation more desirable and noticeable, and add the perception of value. The odor qualities found in this material assist in beautifying and enhancing the finished accord as well as improving the performance of the other materials in the fragrance. There is also the fruity side of it which is found in many fragrances today which happens to be very trendy in vogue, especially for the younger consumers.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, mol is understood to be mole, M is understood to be moles per liter, mmHg be millimeters (mm) of mercury (Hg), and psig is understood to be pound-force per square inch gauge. IFF as used in the examples is understood to mean International Flavors & Fragrances Inc., New York, N.Y., USA.

Example I

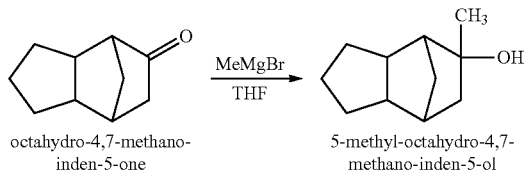

octahydro-4,7-methano-inden-5-one 5-methyl-octahydro-4,7-methano-inden-5-ol

Preparation of 5-methyl-octahydro-4,7-methano-inden-5-ol by Grignard addition

A flame-dried, 5-L 3-necked flask equipped with a mechanical stirrer, an addition funnel condenser, and a thermocouple was charged with methyl magnesium bromide (MeMgBr) in tetrahydrofuran (THF) (3 M, 1.6 L) under nitrogen. The temperature was cooled to and maintained at 15-20° C. using an external isopropyl alcohol (IPA) cooling bath. Octahydro-4,7-methano-inden-5-one (649 g, 4.32 mol) was fed over 3-4 hours. The reaction temperature was allowed to rise to 25-30° C. and maintained at 30° C. for another hour. The reaction mixture was subsequently quenched with acetic acid (HOAc) (279 g, 4.5 mol) and ice. The organic layer was separated to afford the crude product 5-methyl-octahydro-4,7-methano-inden-5-ol (650 g, 90% yield).

$^1$H NMR (CDCl$_3$, 500 MHz): 2.58 ppm (q, 1H, J=8.52 Hz), 1.82-1.94 ppm (m, 4H), 1.77 ppm (s, 1H), 1.74 ppm (s, 1H), 1.63-1.69 ppm (m, 1H), 1.60 ppm (d, 1H, J=12.73 Hz, of d, J=4.68 Hz), 1.39 ppm (d, 1H, J=10.75 Hz, of t, J=1.58 Hz), 1.32 ppm (s, 3H), 1.17-1.30 ppm (m, 2H), 1.11 ppm (d, 1H, J=12.73 Hz, of d, J=3.33 Hz), 0.87-1.00 ppm (m, 2H).

Example II

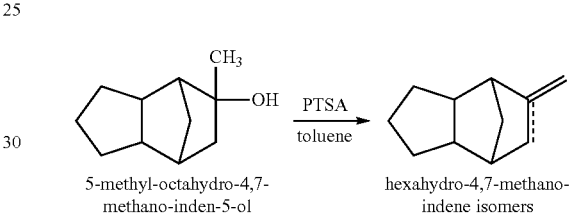

5-methyl-octahydro-4,7-methano-inden-5-ol hexahydro-4,7-methano-indene isomers

Preparation of hexahydro-4,7-methano-indene isomers by dehydration

A 5-L 3-necked flask equipped with a mechanical stirrer, a heating mantel, a condenser, a Bidwell trap, and a thermocouple was charged with 5-methyl-octahydro-4,7-methano-inden-5-ol (650 g, 3.9 mol, synthesized as above in EXAMPLE I). The reaction was heated to 105-110° C. and the THF solvent from the step of EXAMPLE I was distilled. The reaction mixture was then cooled to below 40° C. p-Toluenesulfonic acid (PTSA) (13 g, 2%) and toluene (400 mL) were added in one portion. The reaction mixture was then heated to reflux (~120-135° C.) and water was removed via the Bidwell trap. The reaction was further aged for ~25-30 hours until no more water azeotroped. The resulting reaction mixture was quenched with water (500 mL), washed with sodium carbonate (Na$_2$CO$_3$) (2%, 400 mL), and then transferred to a 5 L distillation flask to be distilled in a rushover unit to afford hexahydro-4,7-methano-indene isomers (533 g, 92% yield), which represent a mixture of 5-methylene-octahydro-4,7-methano-indene and 5-methyl-2,3,3a,4,7,7a-hexahydro-1H-4,7-methano-indene with a boiling point of 130° C. at a pressure of 80 mmHg.

$^1$H NMR (CDCl$_3$, 500 MHz): 4.82 ppm (s, 1H), 4.56 ppm (s, 1H), 2.42 ppm (s, 1H), 2.09-2.15 ppm (m, 1H), 2.07 ppm (s, 1H), 1.77-1.95 ppm (m, 5H), 1.62-1.70 ppm (m, 1H), 1.44 ppm (d, 1H, J=10.00 Hz), 1.15-1.26 ppm (m, 1H), 1.11 ppm (d, 1H, J=10.10 Hz), 0.90-1.00 ppm (m, 2H).

Example III

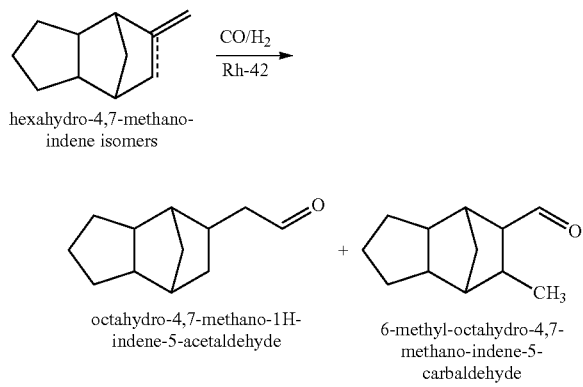

Preparation of octahydro-4,7-methano-1H-indene-5-acetaldehyde (Formula I) and 6-methyl-octahydro-4,7-methano-indene-5-carbaldehyde (Formula II) by hydroformylation A 4 L Zipper Clave was charged with hexahydro-4,7-methano-indene isomers (533 g, 3.6 mol, synthesized as above in EXAMPLE II) and carbonyl hydrido tris(triphenylphosphine)rhodium(I) (Rh-42, commercially available from Johnson Matthey Catalysts, U.S.). The Zipper Clave was flushed and vented three times with nitrogen followed three times with a Syngas mixture of carbon monoxide and hydrogen (50:50 by volume). The Zipper Clave was subsequently pressurized to 300 psig with Syngas and heated to 120° C. Gas-liquid chromatography (GLC) analysis of a reaction aliquot indicated the completion of the reaction after ~2.5 hours. The reaction mixture was then vented and purged three times with nitrogen to provide a crude product, which was distilled to afford a 9:1 mixture of octahydro-4,7-methano-1H-indene-5-acetaldehyde (508.5 g) and 6-methyl-octahydro-4,7-methano-indene-5-carbaldehyde (56.5 g) (88% total yield), which were separated and determined by GC and NMR analysis.

Octahydro-4,7-methano-1H-indene-5-acetaldehyde has the following NMR spectral characteristics:

$^1$H NMR (CDCl$_3$, 500 MHz): 9.76 ppm (t, ~33% of 1H, J=2.1 Hz), 9.73 ppm (t, ~66% of 1H, J=2.1 Hz), 0.85-2.52 (m, 16.66H), 0.57 ppm (m, ~33% of 1H).

Octahydro-4,7-methano-1H-indene-5-acetaldehyde was described as having floral and muguet notes.

6-Methyl-octahydro-4,7-methano-indene-5-carbaldehyde has the following NMR spectral characteristics:

$^1$H NMR (CDCl$_3$, 500 MHz): 9.65 ppm (d, 1H, J=2.0 Hz), 1.01 ppm (d, 3H, J=7.0 Hz), 0.90-2.25 ppm (m, 14H).

6-Methyl-octahydro-4,7-methano-indene-5-carbaldehyde was described as having aldehydic note.

In addition, the mixture of octahydro-4,7-methano-1H-indene-5-acetaldehyde and 6-methyl-octahydro-4,7-methano-indene-5-carbaldehyde (synthesized as above) was evaluated and described as having floral, muguet, aldehydic, green, freesia, sweet, and slightly woody notes.

Example IV

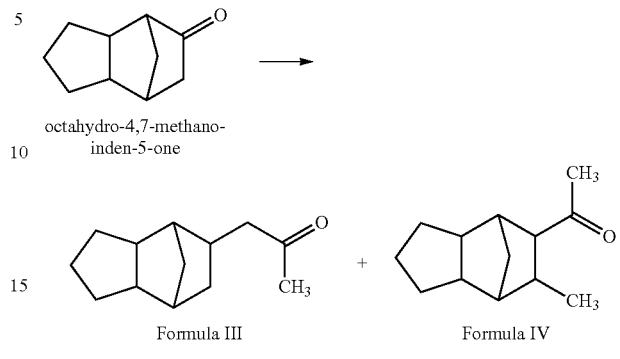

Preparation of 1-(octahydro-4,7-methano-inden-5-yl)-propan-2-one (Formula III) and 1-(6-methyl-octahydro-4,7-methano-inden-5-yl)-ethanone (Formula IV)

1-(Octahydro-4,7-methano-inden-5-yl)-propan-2-one and 1-(6-methyl-octahydro-4,7-methano-inden-5-yl)-ethanone of the above structures were similarly prepared according to EXAMPLEs I-III.

$^1$H NMR (CDCl$_3$, 400 MHz): 2.16-2.52 ppm (m, 2H), 2.11-2.16 ppm (3s, 3H), 1.58-2.06 ppm (m, 8H), 0.47-1.47 ppm (m, 7H).

The mixture of 1-(octahydro-4,7-methano-inden-5-yl)-propan-2-one and 1-(6-methyl-octahydro-4,7-methano-inden-5-yl)-ethanone was described as having floral, fruity, woody, but weak notes with additional metallic character.

Example V

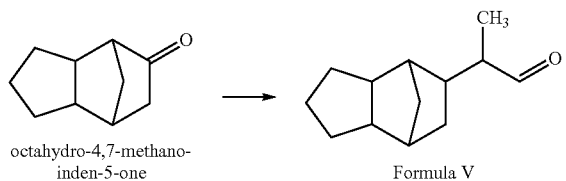

Preparation of 2-(octahydro-4,7-methano-inden-5-yl)-propionaldehyde (Formula V)

2-(Octahydro-4,7-methano-inden-5-yl)-propionaldehyde was similarly prepared according to EXAMPLEs I-III.

$^1$H NMR (CDCl$_3$, 500 MHz): 9.60-9.65 ppm (m, ~30% of 1H), 9.57 ppm (d, ~35% of 1H, J=3.75 Hz), 9.54 ppm (d, ~35% of 1H, J=3.10 ppm), 2.03-2.30 ppm (m, 1H), 1.91-2.03 ppm (m, 2H), 1.68-1.90 ppm (m, 5H), 1.56-1.67 ppm (m, 1H), 1.12-1.49 (m, 4H), 0.66-1.11 ppm (m, 6H).

2-(Octahydro-4,7-methano-inden-5-yl)-propionaldehyde was described as having strong, grapefruit, and offensive sulphury notes.

Example VI

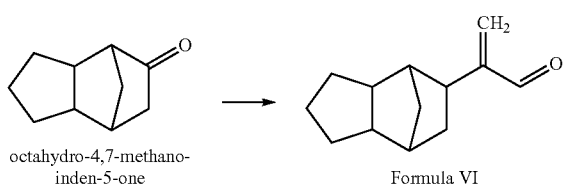

Preparation of 2-(octahydro-4,7-methano-inden-5-yl)-propenal (Structure VI)

2-(Octahydro-4,7-methano-inden-5-yl)-propenal was similarly prepared according to EXAMPLEs I-III.

$^1$H NMR (CDCl$_3$, 500 MHz): 9.56 ppm (s, ~36% of 1H), 9.53 ppm (s, ~64% of 1H), 6.20 ppm (s, ~36% of 1H), 6.18 ppm (s, ~64% of 1H), 6.09 ppm (s, ~36% of 1H), 5.93 ppm (s, ~64% of 1H), 2.92-2.96 ppm (m, ~36% of 1H), 2.43 ppm (s, ~64% of 1H), 1.46-2.25 ppm (m, 6H), 0.86-1.41 ppm (m, 8H).

2-(Octahydro-4,7-methano-inden-5-yl)-propenal was described as having weak, fatty, and green notes.

Example VII

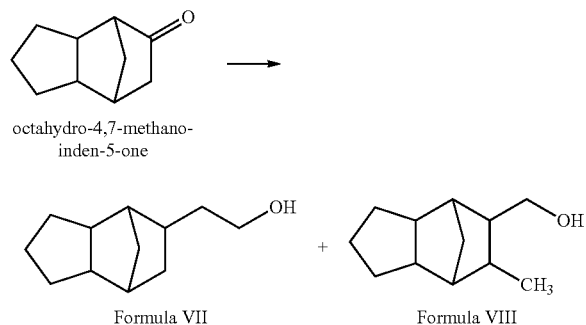

Preparation of 2-(octahydro-4,7-methano-inden-5-yl)-ethanol (Formula VII) and (6-methyl-octahydro-4,7-methano-inden-5-yl)-methanol (Formula VIII)

2-(Octahydro-4,7-methano-inden-5-yl)-ethanol and (6-methyl-octahydro-4,7-methano-inden-5-yl)-methanol were similarly prepared according to EXAMPLEs I-III with further hydrogenation.

$^1$H NMR (CDCl$_3$, 500 MHz): 3.63 ppm (t, ~89% of 2H, J=7.00 Hz), 3.38-3.48 ppm (m, ~11% of 2H), 1.66-2.20 ppm (m, 7H), 1.51-1.65 ppm (m, 2H), 1.30-1.50 ppm (m, 3H), 0.53-1.28 ppm (m, 6H).

The mixture of 2-(octahydro-4,7-methano-inden-5-yl)-ethanol and (6-methyl-octahydro-4,7-methano-inden-5-yl)-methanol was described as having very weak and woody notes.

Example VIII

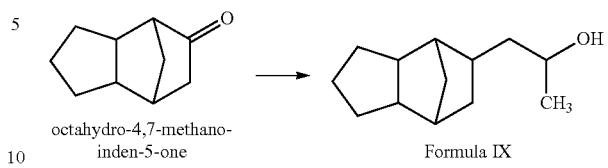

Preparation of 1-(octahydro-4,7-methano-inden-5-yl)-propan-2-ol (Formula IX)

1-(Octahydro-4,7-methano-inden-5-yl)-propan-2-ol was similarly prepared according to EXAMPLEs I-III with further hydrogenation.

$^1$H NMR (CDCl$_3$, 400 MHz): 3.74-3.86 ppm (m, ~89% of 1H), 3.41-3.56 ppm (m, ~11% of 1H), 1.25-2.18 ppm (m, 12H), 1.07-1.24 ppm (m, 5H), 0.50-1.06 ppm (m, 4H).

1-(Octahydro-4,7-methano-inden-5-yl)-propan-2-ol was described as having very weak, green, floral, and fruity notes with additional harsh character.

Example IX

The fragrance formulas exemplified as follows demonstrated that the addition of the mixture of octahydro-4,7-methano-1H-indene-5-acetaldehyde and 6-methyl-octahydro-4,7-methano-indene-5-carbaldehyde (synthesized as above) provided floral, muguet, aldehydic, green, freesia, sweet, and slightly woody notes to the fragrance formula:

| Ingredient | Parts (grams) | Parts (grams) |
|---|---|---|
| ALD C-10 PRG STABILIFF | 0.208 | 0.208 |
| PATCHOULI OIL LIGHT BLO | 2.079 | 2.079 |
| DIHYDRO SEVENIFF | 10.395 | 10.395 |
| ALLYL AMYL GLYCOLATE PRG BHT | 0.520 | 0.520 |
| DAMASCONE DELTA BHT | 0.104 | 0.104 |
| GALAXOLIDE 50 PCT BENZ SAL | 5.198 | 5.198 |
| CLOVE LEAF OIL RECT BLO | 0.208 | 0.208 |
| POLYSANTOL (ELINCS) | 1.040 | 1.040 |
| KOAVONE | 5.198 | 5.198 |
| CYCLACET PRG | 10.395 | 10.395 |
| ISO CYCLEMONE E BHT | 10.395 | 10.395 |
| GRAPEFRUIT OIL RECT | 2.079 | 2.079 |
| NEBULONE (ELINCS) | 5.198 | 5.198 |
| PERANAT | 0.520 | 0.520 |
| POIRENATE (ELINCS) | 0.520 | 0.520 |
| VERDOX | 1.040 | 1.040 |
| BENZ ACET PRG | 2.079 | 2.079 |
| VERIDIAN | 1.040 | 1.040 |
| VANILLIN PRG | 0.208 | 0.208 |
| LAVANDIN GROSSO OIL LMR | 3.119 | 3.119 |
| LIMONENE VAH "PFG" BHT | 2.079 | 2.079 |
| VERTOFIX COEUR | 5.198 | 5.198 |
| GALAXOLIDE SUPER 50 PCT IPM | 5.198 | 5.198 |
| VERTENEX HC | 5.198 | 5.198 |
| FORMULA I/FORMULA II | 5.198 | — |
| DIPROPYLENE GLYCOL | — | 5.198 |
| CYCLAAL TOCO | 15.198 | 15.198 |
| METH DH JASMONATE BHT | 10.395 | 10.395 |
| Total | 110.007 | 110.007 |

Example X

The differences in odor profiles of octahydro-4,7-methano-1H-indene-5-acetaldehyde (Formula I) and 6-methyl-octahydro-4,7-methano-indene-5-carbaldehyde (Formula II) and their analogs (Formulas III-IX) are listed in the following:

| Compounds | Odor Profiles |
|---|---|
| Formula I and Formula II | Floral, muguet, aldehydic, green, freesia, sweet, and slightly woody |
| Formula III and Formula IV | Floral, fruity, woody, weak, and metallic |
| Formula V | Strong, grapefruit, and offensive sulphury |
| Formula VI | Weak, fatty, and green |
| Formula VII and Formula VIII | Very weak and woody |
| Formula IX | Very weak, green, floral, fruity, and harsh |

The above evaluation demonstrated that the mixture of Formula I and Formula II displayed highly desirable properties, which are absent in the analogs of similar structures. The advantageous and distinctive properties of Formula I and Formula II are unexpected and would not have been predicted.

What is claimed is:

1. A compound, octahydro-4,7-methano-1H-indene-5-acetaldehyde.

2. A fragrance formulation containing an olfactory acceptable amount of octahydro-4,7-methano-1H-indene-5-acetaldehyde.

3. The fragrance formulation of claim 2 further comprising a product selected from the group consisting of a perfume, a cologne, toilet water, a cosmetic product, a personal care product, a fabric care product, a cleaning product, and an air freshener.

4. The fragrance formulation of claim 3, wherein the cleaning product is selected from the group consisting of a detergent, a dishwashing composition, a scrubbing compound, and a window cleaner.

5. The fragrance formulation of claim 2, wherein the olfactory acceptable amount is from about 0.005 to about 50 weight percent of the fragrance formulation.

6. The fragrance formulation of claim 2, wherein the olfactory acceptable amount is from about 0.5 to about 25 weight percent of the fragrance formulation.

7. The fragrance formulation of claim 2, wherein the olfactory acceptable amount is from about 1 to about 10 weight percent of the fragrance formulation.

8. A method of improving, enhancing or modifying a fragrance formulation through the addition of an olfactory acceptable amount of octahydro-4,7-methano-1H-indene-5-acetaldehyde.

9. The method of claim 8, wherein the olfactory acceptable amount is from about 0.005 to about 50 weight percent of the fragrance formulation.

10. The method of claim 8, wherein the olfactory acceptable amount is from about 0.5 to about 25 weight percent of the fragrance formulation.

11. The method of claim 8, wherein the olfactory acceptable amount is from about 1 to about 10 weight percent of the fragrance formulation.

12. A fragrance product comprising the compound of claim 1.

* * * * *